United States Patent
Weyl et al.

(10) Patent No.: US 6,613,206 B1
(45) Date of Patent: Sep. 2, 2003

(54) GAS SENSOR

(75) Inventors: Helmut Weyl, Schwieberdingen (DE); Hans-Martin Wiedenmann, Stuttgart (DE); Theodor Graser, Stuttgart (DE); Karl-Heinz Effenberger, Schwaebisch Gmuend (DE); Clemens Simon, Starnberg (DE); Anton Hans, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/308,078

(22) PCT Filed: Sep. 4, 1998

(86) PCT No.: PCT/DE98/02608

§ 371 (c)(1),
(2), (4) Date: Jul. 14, 1999

(87) PCT Pub. No.: WO99/14583

PCT Pub. Date: Mar. 25, 1999

(30) Foreign Application Priority Data

Sep. 13, 1997 (DE) .......................................... 197 40 363

(51) Int. Cl.[7] ............................................. G01N 27/407
(52) U.S. Cl. ........................ 204/424; 204/421; 204/426
(58) Field of Search ................................. 204/421–429

(56) References Cited

U.S. PATENT DOCUMENTS

| 4,152,232 A | 5/1979 | Otsuka et al. | |
| 4,334,974 A | * 6/1982 | Muller et al. | 204/425 |
| 4,588,494 A | * 5/1986 | Kato et al. | 204/426 |
| 5,246,562 A | * 9/1993 | Weyl et al. | 204/428 |
| 6,082,175 A | * 7/2000 | Yoshikawa et al. | 204/426 |
| 6,083,371 A | * 7/2000 | Weyl et al. | 204/428 |

FOREIGN PATENT DOCUMENTS

| DE | 42 04 850 | 8/1993 |
| DE | 195 49 283 | 6/1997 |

OTHER PUBLICATIONS

"Silicon Nitride Ceramic Spring", NHK International Corporation.*

Fitzgerald et al, "Basic Electrical Engineering" 2d ed., (1957) Month Unavailable pp. 168,169,181.*

* cited by examiner

Primary Examiner—T. Tung
(74) Attorney, Agent, or Firm—Kenyon & Kenyon

(57) ABSTRACT

A gas sensor, in particular a lambda probe, for ascertaining the pollutant and/or oxygen content in emission gases of internal combustion engines, having a housing accommodating at least one sensor element, the sensor element having a section on the terminal side and a section on the measuring-gas side, and having a connecting element that connects the sensor element, which has a plurality of electrically conductive contact areas, at its terminal-side section to a plurality of electrically conductive supply leads. The gas sensor has the feature of a connecting element which is formed from a spring element produced in one piece from ceramic material.

11 Claims, 2 Drawing Sheets

GAS SENSOR

FIELD OF THE INVENTION

The a gas sensor, in particular a lambda probe, for ascertaining the pollutant and/or oxygen content in emission gases of internal combustion engines.

BACKGROUND INFORMATION

German Patent Application No. 42 04 850 describes a gas sensor which has a housing used for accommodating a sensor element. The sensor element has a section on the terminal side and a section on the measuring-gas side. Using a connecting element, the sensor element, having a plurality of electrically conductive contact areas, is connected at its terminal-side section to electrically conductive supply leads. The connecting element is composed of two sections held together by a sleeve, between which the sensor element and the supply leads are immovably retained. Because several parts are necessary for the connections of the supply leads to the sensor element, the assembly of the gas sensor, in particular the connection of the gas sensor to the supply leads, is costly. In addition, the production costs of the multi-part connecting element are high.

SUMMARY OF THE INVENTION

The gas sensor of the present invention, has the distinction that the connecting element is formed from a spring element produced in one piece from ceramic material. Because the spring element is designed in one piece, it can be produced very simply, and thus cost-effectively, using, for example, the extrusion method, therefore in just one procedure. The sensor element and the supply leads are frictionally connected to one another by the spring element which can be easily mounted. To that end, first the connectors are introduced into or extended through a feed-through opening of the preferably ring-shaped spring element, and the sensor element is subsequently fixed in position and retained by sliding on the spring element. Alternatively, it is also possible to insert the sensor element into the feed-through opening or optionally, to mount it by pressing. The assembly can be accomplished simply and quickly for both embodiment variants. The spring element makes it possible to realize a great contact force acting in the radial direction between the supply leads, the sensor element and the spring element. Due to the small mass of the spring element, the sensor element is only slightly dynamically stressed, i.e., in the event of vibration, only a small deflection takes place.

In one exemplary embodiment of the gas sensor, at least one slit is introduced into the feed-through opening of the spring element. This makes it possible to realize a great spring excursion of the spring element produced from ceramic material. When slipping the spring element onto the sensor element, or when inserting the sensor element into the feed-through opening of the spring element, the spring element is spread. This ensures that the supply leads will not be shifted, at least substantially, when forming the frictional connection, and their position will be maintained within the feed-through opening. However, it is also possible to initially mechanically spread the spring element before assembly, thus before the connection of the supply leads to the sensor element, and only then to form the frictional connection by slipping the spring element onto the sensor element and/or inserting the sensor element into the spring element. This permits a—at least essentially—nearly force-free connection of the sensor element to the supply leads. The "force-free connection" is referring to the slipping of the spring element onto the sensor element and/or the insertion of the sensor element into the feed-through opening.

Furthermore, another exemplary embodiment of the gas sensor which provides a feature that the feed-through opening has a plurality of—preferably curve-shaped—depressions running at least essentially in the longitudinal direction of the spring element. The electrically conductive supply leads are pressed by the sensor element into the depressions and are held therein by jamming. This ensures that, after the spring element is mounted, the supply leads are immovably retained in the depressions, thus making it possible to virtually rule out a mutual contacting of the supply leads after the assembly—at least in the area of the spring element. The number of depressions can be in the range between two and eight. In one especially preferred exemplary embodiment, a total of four depressions are provided in the feed-through opening.

In another exemplary embodiment, the spring element includes a plurality of connectors, each having at least one electrically conductive contact area, to which the supply leads can be attached before or after the spring element is mounted. Understood by attaching is both an integral joining, for example, by a welded connection, as well as a frictional connection, for example, a crimped connection. Because the spring element is fitted with the supply leads before the assembly, the assembly time of the gas sensor can be reduced.

According to another exemplary embodiment, the connectors are inserted into the feed-through opening. The connectors are preferably designed in such a way that in the assembled state of the spring element, a form-locking fit is ensured between the spring element and the connectors. In another exemplary embodiment, the connectors are molded into the spring element, i.e., they are inserted into the ceramic material during the production of the spring element, and are thereby embedded. In both variants of the embodiment, it is possible to spread the supply leads. The isolation of the supply leads in the area of the spring element is effected by the spring element.

DETAILED DESCRIPTION

Figure 1:
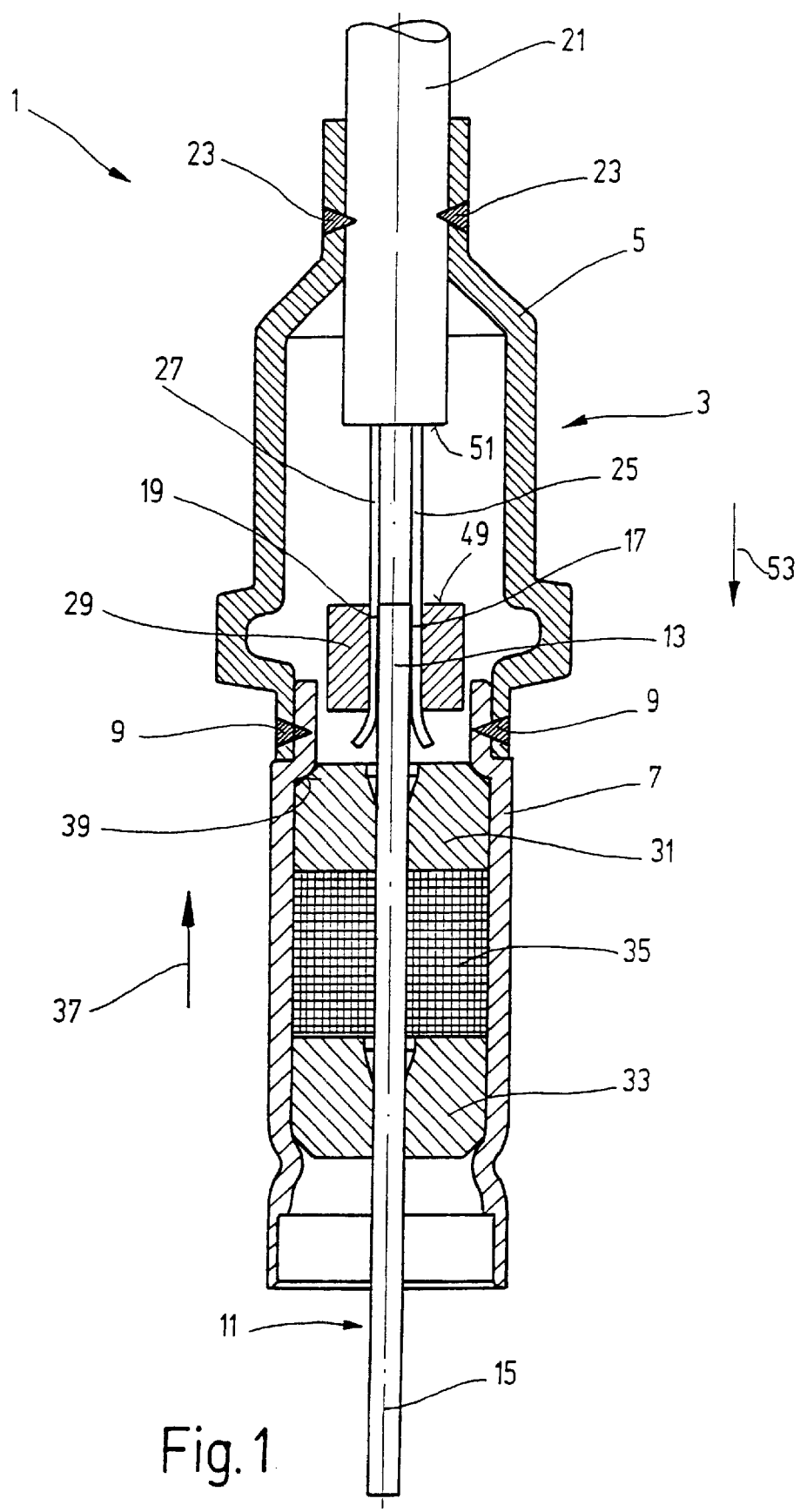
FIG. 1 shows a schematic, longitudinal sectional view of an exemplary embodiment of the gas sensor according to the present invention.

FIG. 1 shows a longitudinal section of a first exemplary embodiment of a gas sensor 1, e.g., a lambda probe, for ascertaining the pollutant and/or oxygen content in emission gases of internal combustion engines, which includes a protective housing 3 formed by two sleeve-shaped housing parts 5 and 7. They are welded together, only welding spots 9 of the welding spots being shown in FIG. 1. In another exemplary embodiment, protective housing 3 is designed in one piece, i.e., housing parts 5, 7 already form one unit before gas sensor 1 is assembled. Housing part 7 is used to accommodate a planar sensor element 11, which has a terminal-side section 13 and a measuring-gas-side section 15. Sensor element 11, exhibiting in this exemplary embodiment a rectangular cross-section, has a plurality of contact areas in the region of section 13, of which only contact areas 17 and 19 are shown in FIG. 1.

Gas sensor 1 further includes a metal tube 21, also designated as a metal-sheathed cable, which is joined, in this case by welding, to first housing part 5 of protective housing 3, as is indicated by welding spots 23. Metal tube 21 can also already be joined to first housing part 5, forming one unit, before gas sensor 1 is assembled. Arranged inside metal tube 21, set apart from each other, are a number of electrically conductive supply leads which are embedded in an insulating material such as magnesium oxide. The metal tube can have up to eight supply leads. In this exemplary embodiment, provision has been made for a total of four supply leads, of which only supply leads 25 and 27 are discernible in the sectional view of FIG. 1. The metal tube 21, that is to say supply leads 25, 27 are frictionally connected to sensor element 11 by a connecting element 29. Connecting element 29 is further described with reference to FIGS. 2 through 4.

Arranged inside first housing part 7 are insulating bushings 31 and 33, between which a porous packing 35 is jammed. Insulating bushings 31,33 and packing 35 are introduced into second housing part 7 from the side of second housing part 7 facing measuring-gas-side section 15 of sensor element 11 and are acted upon by compressive force operating in the direction of an arrow 37. In the process, insulating bushing 31 is positioned against a circumferential annular shoulder 39 of second housing part 7 and is braced against it, so that insulating bushings 31,33 and packing 35 are compressed and sensor element 11, extending through the longitudinal bore hole, is held by jamming. To fix the parts in position, second housing part 7 is subsequently squeezed from the outside, so that its inside diameter becomes smaller.

Figure 2:
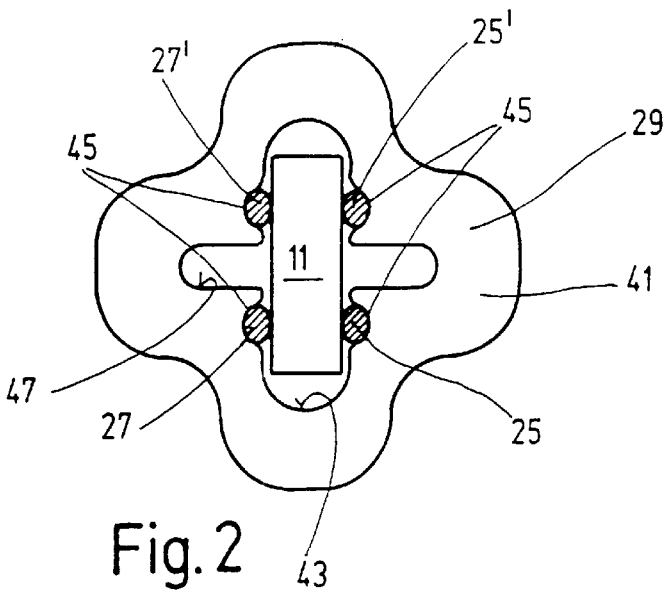
FIG. 2 shows a top view of a first exemplary embodiment of a connecting element of the gas sensor illustrated in FIG. 1.

FIG. 2 shows a top view of a first exemplary embodiment of connecting element 29, which is formed from a spring element 41 produced in one piece from ceramic material. It is ring-shaped, and has here an essentially rectangular feed-through opening 43. The annular body of spring element 41 is closed, that is to say, the wall of the ring is not slitted. Introduced into feed-through opening 43 are a plurality, in this case a total of four depressions 45 which run essentially in the longitudinal direction of spring element 41. Thus, depressions 45 lie in a plane which is essentially normal to the image plane of FIG. 2. The groove-type depressions 45 have a curve-shaped, in this case a semicircular contour, and are used for accommodating supply leads 25, 25', 27 and 27'. As can be seen from FIG. 2, supply leads 25, 25', 27, 27' each lie in one depression 45, or rather are pressed by sensor element 11 into the depressions. Also introduced in feed-through opening 43 is a slit 47, running transversely to the longitudinal extension of feed-through opening 43, the slit being used to increase the excursion of spring element 41. Given a spring element having an outside diameter of approximately 6 mm and a thickness of approximately 4.5 mm, the spring excursion can be up to 1/10 mm and more.

The shape of feed-through opening 43 is variable, and in another exemplary embodiment, can also be circular. Preferably, the shape of the feed-through opening corresponds —at least substantially—to the shape of sensor element 11, which can also have a quadratic cross-section, for example.

In the following, the functioning of spring element 41 is explained in more detail in the light of an assembly process:

First of all, supply leads 25, 25', 27, 27' are passed or inserted through feed-through opening 43 of spring element 41, and spring element 41 is pushed right against metal tube 21, so that end face 49 of spring element 41 abuts against front end 51 of metal tube 21. Then sensor element 11 is placed in position at feed-through opening 43, and spring element 41 is slipped or pressed onto sensor element 11 in the direction of arrow 53 shown in FIG. 1. In so doing, supply leads 25, 35 25', 27, 27' are pressed into their respective depression 45 and are retained there by jamming. By sliding spring element 41 onto sensor element 11, the supply leads are fixed in position, and at the same time the contacting is produced between the contact areas of sensor element 11, which are not shown in FIG. 2, and the supply leads. Spring element 41 is spread when being slipped on.

Depressions 45 are constructed in such a way that supply leads 25, 25', 27, 27' are not completely accommodated by the depressions when being pressed into them during the mounting of sensor element 11, so that in the assembled state, a force acting in the radial direction operates between the supply leads, the spring element and the sensor element.

In another exemplary embodiment, sensor element 11 is introduced into feed-through opening 43, that is to say, spring element 41 is not shifted for the connection of the supply leads to sensor element 11, but is merely retained. Of course, it is also possible that spring element 41 is slipped onto sensor element 11 for the connection of the supply leads to sensor element 11, and in so doing, sensor element 11 is simultaneously inserted into feed-through opening 43.

Spring element 41 can be mechanically spread before the assembly, so that when slipping spring element 41 onto sensor element 11, or when inserting sensor element 11 into feed-through opening 43, virtually no, or at least only very slight force must be applied. The force-free assembly prevents a relative movement of the supply leads arranged in feed-through opening 43.

In the exemplary embodiment of the gas sensor shown in FIG. 1, after the connection with sensor element 11, the supply leads can be pulled a bit in the direction of metal tube 21, out of the feed-through opening. Consequently, stress of the supply leads in response to tension is avoided.

Figure 3:
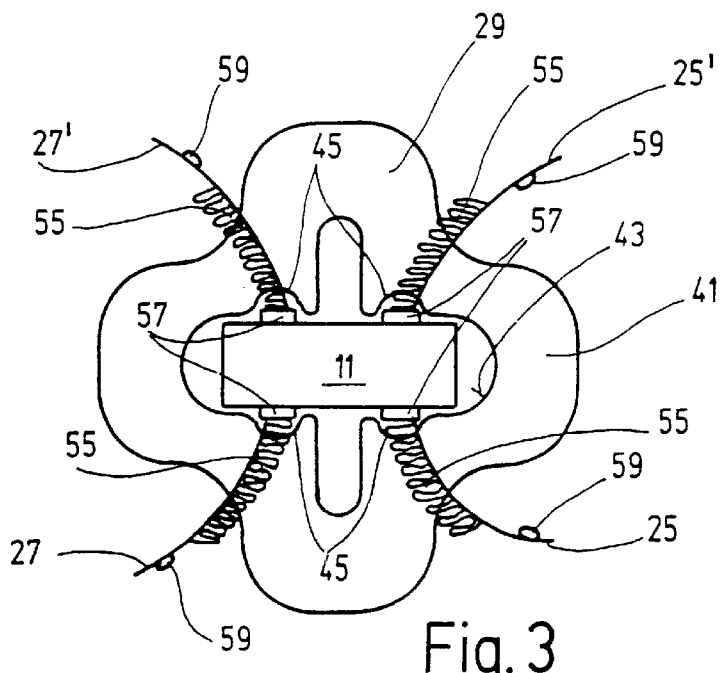
FIG. 3 shows a top view of a second exemplary embodiment of the connecting element.

FIG. 3 shows a top view of a further exemplary embodiment of spring element 41. The same parts are provided with the same reference numerals, so that in this respect, reference is made to the description of FIG. 1. In the following, only the differences shall be discussed in more detail. Arranged in each depression 45 of spring element 41 is one connector 55 which has an electrically conductive contact area 57. Secured to each connector 55 is one supply lead 25, 25', 27, 27', for example welded on or retained by a crimped connection, as is indicated by an enlargement 59. Connectors 55 can be inserted into feed-through opening 43 of ceramic spring element 41, or can be molded during its production. Supply leads 25, 25', 27, 27' are secured to connectors 55 before the connection to sensor element 11 in order to avoid pre-damage to contact areas 57 and the contact areas of sensor element 11, which are not shown in FIG. 3, for example, because of heat which is too great when welding on the supply leads.

In another exemplary embodiment, spring element 41 has only a feed-through opening 43 without depressions, so that when connectors 55 have been inserted, a form-locking fit is realized between them and spring element 41.

Figure 4:
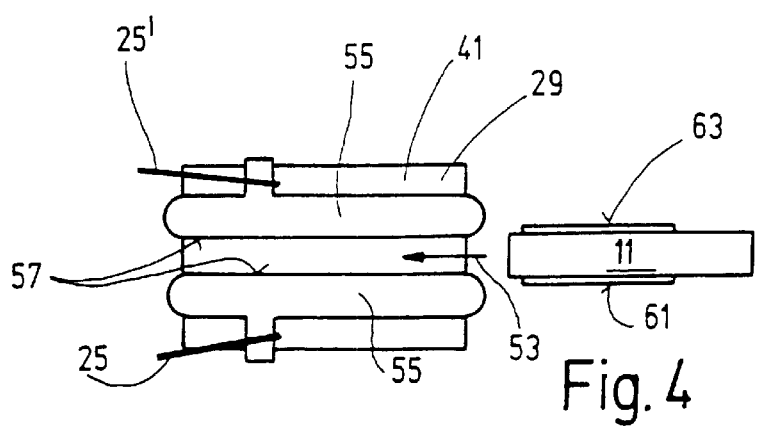
FIG. 4 shows a longitudinal section through a third exemplary embodiment of the connecting element.

FIG. 4 shows a longitudinal section of a third exemplary embodiment of spring element 41 and a second exemplary embodiment of connectors 55. Connectors 55 are insertable into feed-through opening 43 of spring element 41, or can be molded into the spring element. Connectors 55 extend through the entire feed-through opening 43 and beyond it.

As shown in FIG. 4, in this case the supply leads, of which only supply leads 25, 25' are shown, are connected to sensor element 11 by inserting sensor element 11 into feed-through opening 43. In the assembled state, one contact area 61 of sensor element 11 abuts against contact area 57 of connector 55 joined to supply lead 25, and a further contact area 63 abuts against contact area 57 of connector 55 joined to supply lead 25'.

In the exemplary embodiments described with reference to FIGS. 3 and 4, the supply leads can be spread in the assembled state, in order to prevent mutual contacting.

In summary, the spring element, produced in one piece from ceramic material, makes it possible to connect supply leads 25, 25'27, 27' to the sensor element very easily, and therefore cost-effectively. The individual supply leads are isolated from one another by electrically non-conductive spring element 41.

What is claimed is:

1. A gas sensor for determining at least one of a pollutant content and an oxygen content in an emission gas of an internal combustion engine, comprising:
   at least one sensor element having a terminal side section and a measuring gas side section, the at least one sensor element including a plurality of electrically conductive contact areas;
   a housing accommodating the at least one sensor element;
   a plurality of electrically conductive supply leads; and
   a one-piece spring element composed of a ceramic material, the one-piece spring element coupling the terminal side section of the at least one sensor element to the electrically conductive supply leads.

2. The gas sensor according to claim 1, wherein the spring element has a ring shape.

3. The gas sensor according to claim 1, wherein the spring element includes a plurality of connectors, each of the connectors having at least one respective electrically conductive contact area.

4. The gas sensor according to claim 3, wherein the spring element has a feed-through opening, and wherein the connectors are one of insertable and molded into the feed-through opening.

5. The gas sensor according to claim 1, wherein, when the spring element is assembled, further contact areas of the electrically conductive supply leads abut against the electrically conductive contact areas of the at least one sensor element.

6. The gas sensor according to claim 1, wherein the gas sensor includes a lambda probe.

7. A gas sensor for determining at least one of a pollutant content and an oxygen content in an emission gas of an internal combustion engine, comprising:
   at least one sensor element having a terminal side section and a measuring gas side section, the at least one sensor element including a plurality of electrically conductive contact areas;
   a housing accommodating the at least one sensor element;
   a plurality of electrically conductive supply leads; and
   a connecting element coupling the terminal side section of the at least one sensor element to the electrically conductive supply leads, the connecting element including a one-piece spring element composed of a ceramic material;
   wherein the spring element has a ring shape;
   wherein the spring element has a feed-through opening, and wherein at least one slit is introduced into the feed-through opening.

8. The gas sensor to claim 7, wherein the feed-through opening has a plurality of depressions which extend in a substantially longitudinal direction of the spring element.

9. The gas sensor according to claim 8, wherein the depressions have a curved shape.

10. The gas sensor according to claim 8, wherein a number of the depressions is between two and eight.

11. The gas sensor according to claim 8, wherein the feed-through opening has four depressions.

\* \* \* \* \*

UNITED STATES PATENT AND TRADEMARK OFFICE
CERTIFICATE OF CORRECTION

PATENT NO. : 6,613,206 B1
DATED : September 2, 2003
INVENTOR(S) : Weyl et al.

It is certified that error appears in the above-identified patent and that said Letters Patent is hereby corrected as shown below:

Column 1,
Line 5, change "a" to -- present invention relates to a --.
Line 28, delete ",".

Signed and Sealed this

Twenty-seventh Day of July, 2004

JON W. DUDAS
*Acting Director of the United States Patent and Trademark Office*